(12) United States Patent
Kuroda et al.

(10) Patent No.: US 9,273,290 B2
(45) Date of Patent: Mar. 1, 2016

(54) METHOD FOR PRODUCING PHOSPHITE DEHYDROGENASE PROTEIN AND USE THEREOF

(75) Inventors: Akio Kuroda, Higashi-Hiroshima (JP); Ryuichi Hirota, Higashi-Hiroshima (JP)

(73) Assignee: HIROSHIMA UNIVERSITY, Higashi-Hiroshima (JP)

( * ) Notice: Subject to any disclaimer, the term of this patent is extended or adjusted under 35 U.S.C. 154(b) by 168 days.

(21) Appl. No.: 14/113,346

(22) PCT Filed: Apr. 16, 2012

(86) PCT No.: PCT/JP2012/060293
§ 371 (c)(1),
(2), (4) Date: Oct. 22, 2013

(87) PCT Pub. No.: WO2012/147556
PCT Pub. Date: Nov. 1, 2012

(65) Prior Publication Data
US 2014/0051134 A1 Feb. 20, 2014

(30) Foreign Application Priority Data

Apr. 26, 2011 (JP) ................................. 2011-098670

(51) Int. Cl.
C12N 9/04 (2006.01)
C12P 17/18 (2006.01)
C12N 9/02 (2006.01)
(52) U.S. Cl.
CPC ............ *C12N 9/0006* (2013.01); *C12N 9/0004* (2013.01); *C12P 17/182* (2013.01); *C12Y 120/01001* (2013.01)
(58) Field of Classification Search
None
See application file for complete search history.

(56) References Cited

U.S. PATENT DOCUMENTS

2004/0091985 A1* 5/2004 Metcalf et al. ................ 435/189
2005/0026250 A1* 2/2005 Zhao et al. .................... 435/69.1
2010/0151529 A1* 6/2010 Zhao et al. ..................... 435/90

FOREIGN PATENT DOCUMENTS

WO  WO 2004108912 A2 * 12/2004
WO  WO 2006074194 A2 *  7/2006
WO  WO 2008131215 A2 * 10/2008

OTHER PUBLICATIONS

Woodyer et al., "Site-directed mutagenesis of active site residues of phosphite dehydrogenase", Biochemistry, vol. 44, pp. 4765-4774, 2005.*
GenBank Accession No. AAT12779.1, published Jan. 7, 2005.*
GenBank Accession No. BAB77417.1, published Mar. 12, 2009.*
UniProt ID E2SZ28_9RALS, available Jan. 11, 2011.*
Database GenBank (online), Apr. 19, 2011 uploaded, Accession No. CP002657, Definition:*Alicycliphilus denitrificans* K601, complete genome[retrieved on Apr. 27, 2012] Retrieved from the Internet: <URL:http://www.ncbi.nlm.nih.gov/nuccore/329308025?sat= 14&satkey=10503485>.

(Continued)

*Primary Examiner* — Tekchand Saidha
*Assistant Examiner* — Richard Ekstrom
(74) *Attorney, Agent, or Firm* — Casimir Jones, SC

(57) ABSTRACT

In order to provide: a phosphite dehydrogenase protein having both improved solubility and improved heat stability; a method for producing a gene encoding the phosphite dehydrogenase protein; a method for producing the phosphite dehydrogenase protein; and use of the phosphite dehydrogenase protein, (i) a phosphite dehydrogenase protein having a specific amino acid sequence and (ii) a gene encoding the phosphite dehydrogenase protein are used.

10 Claims, 3 Drawing Sheets

(56) References Cited

OTHER PUBLICATIONS

Database GenBank [online], Oct. 18, 2010 uploaded, Accession No. EFP65990, Definition: phosphonate dehydrogenase (NAD-dependent phosphitedehydrogenase) [Ralstonia sp. 5_7_47FAA] [retrieved on Apr. 27, 2012] retrieved from the Internet: <URL:http://www.ncbi.nlm.nih.gov/protein/efp65990>.

Fujibuchi, et al., "12Kp13: Identification and characterization of phosphite dehydrogenase," Proceedings of the Annual Meeting of the Society for Biotechnology, Japan, Aug. 25, 2011, vol. 63, p. 193.

Garcia Costas, A.M.,. et al., "Purification and Characterization of a Novel Phosphorus-oxidizing Enzyme from *Pseudomonas stutzeri* WM88," J. Biol. Chem. (2001), vol. 276, pp. 17429-17436.

Hirota, R., et al., "Isolation and characterization of a soluble and thermostable phosphite dehydrogenase from Ralstonia sp. Strain 4506," J. Biosci. Bioeng. (2012), vol. 113, No. 4, pp. 445-450, Epub. Dec. 23, 2011.

Hirota, Ryuichi, et al., "2kp19: Construction and characterization of an NADH regeneration system using phosphite dehydrogenase," Proceedings of the Annual Meeting of the Society for Biotechnology, Japan, Aug. 25, 2011, vol. 63, p. 194.

International Search Report mailed May 15, 2012, International Patent Application No. PCT/JP2012/060293.

Johannes, T.W., et al., "Directed Evolution of a Thermostable Phosphite Dehydrogenase for NAD(P)H Regeneration," Applied and Environmental Microbiology (2005), vol. 71, No. 10, pp. 5728-5734.

Johannes, T.W., et al., "Efficient Regeneration of NADPH Using an Engineered Phosphite Dehydrogenase", Biotechnol. Bioeng. (2007), vol. 96, No. 1, pp. 18-26.

Kuroda, Akio, et al., "2S3p01: Biotechnology for utilizing reduced phosphorus compounds," Proceedings of the Annual Meeting of the Society for Biotechnology, Japan, Aug. 25, 2011, vol. 63, p. 93.

McLachlan, M.J., et al., "Further Improvement of Phosphite Dehydrogenase Thermostability by Saturation Mutagenesis," Biotechnology and Bioengineering (2008), vol. 99, Issue 2, pp. 268-274.

Vrtis, Jennifer M., et al., "Phosphite Dehydrogenase: A Versatile Cofactor-Regeneration Enzyme," Angew. Chem. Int. Ed. (2002), 41, No. 17, pp. 3257-3259.

Woodyer, R., et al., "Mechanistic investigation of a highly active phosphite dehydrogenase mutant and its application for NADPH regeneration," FEBS J. (2005), vol. 272, No. 15, pp. 3816-3827.

Woodyer, R., et al., "Optimizing a Biocatalyst for Improved NAD(P)H Regeneration: Directed Evolution of Phosphite Dehydrogenase," Combinatorial Chemistry & High Throughput Screening (2006), vol. 9, No. 4, pp. 237-245.

English translation of the International Preliminary Report on Patentability (Chapter II) of PCT Application No. PCT/JP2012/060293 mailed Oct. 31, 2013.

\* cited by examiner

METHOD FOR PRODUCING PHOSPHITE DEHYDROGENASE PROTEIN AND USE THEREOF

CROSS REFERENCE TO RELATED APPLICATIONS

The present application is a U.S. 371 National Stage Entry of pending International Patent Application No. PCT/JP2012/060293, international filing date Apr. 16, 2012, which claims priority to JP Patent Application No. 2011-098670, filed Apr. 26, 2011, the contents of which are incorporated by reference in their entireties.

TECHNICAL FIELD

The present invention relates to a method for producing a phosphite dehydrogenase protein, and a use of the phosphite dehydrogenase protein. More specifically, the present invention relates to the method for producing the phosphite dehydrogenase protein, a method for producing NADH, and a method for producing NADPH.

BACKGROUND ART

A phosphite dehydrogenase protein (PtxD) is a protein which exists in some bacteria and is an enzyme which oxidizes phosphorous acid in an $NAD^+$-dependent or $NADP^+$-dependent manner to generate NADH or NADPH. The following are reaction formulae respectively corresponding to a case where phosphorous acid is oxidized in an $NAD^+$-dependent manner and a case where phosphorous acid is oxidized in an $NADP^+$-dependent manner.

[Chem. 1]
Catalyst: PtxD

$HPO_3^{2-}+NAD^++H_2O \rightarrow HPO_4^{2-}+NADH+H^+$ (Reaction formula 1)

[Chem. 2]
Catalyst: PtxD

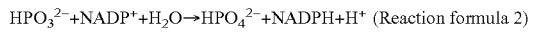

$HPO_3^{2-}+NADP^++H_2O \rightarrow HPO_4^{2-}+NADPH+H^+$ (Reaction formula 2)

The above chemical reactions are expected as being highly potential because they allow efficient production of NADH or NADPH, each of which functions as a very important cofactor in production of a substance with use of a biological reaction. However, industrial use of the chemical reactions has not been developed yet. That is, at present, industrial mass-production of NADH or NADPH with use of phosphorous acid has not been realized (see, for example, Non-patent Literatures 1 and 2). Enzymes such as formic dehydrogenase, glucose dehydrogenase, alcohol dehydrogenase, and the like have conventionally been used for production of NADH and NADPH. However, since the enzymes use a highly reactive substrate, a reaction system thereof is unstable. Further, the enzymes yield a highly reactive product. This also makes the reaction system thereof unstable. Note, here, that a main cause for making the reaction system unstable is changes in pH. On the other hand, phosphite dehydrogenase is advantageous not only in that phosphite dehydrogenase uses a weakly reactive substrate and yields a weakly reactive product, but also in that the substrate used by phosphite dehydrogenase is inexpensive. Phosphite dehydrogenase therefore has a potential to be widely used in place of the above enzymes, if industrial use of phosphite dehydrogenase is realized. Specifically, in a case where phosphite dehydrogenase is used, a reaction system can be stabilized, since both phosphorous acid and phosphoric acid have a buffering action.

In order to produce NADH and NADPH in large quantities industrially, a large amount of the phosphite dehydrogenase protein is required. As such, it has conventionally been tried to obtain a large amount of the phosphite dehydrogenase protein by (i) forcibly causing expression of a heterologous organism-derived wild-type phosphite dehydrogenase protein in a host such as *Escherichia coli* and (ii) then purifying the wild-type phosphite dehydrogenase protein.

However, according to the technique, a large part of the wild-type phosphite dehydrogenase protein becomes insoluble in an aqueous solution when the wild-type phosphite dehydrogenase protein is forcibly expressed in *E. coli* or the like. This makes it impossible to collect the wild-type phosphite dehydrogenase protein. As such, there is a demand for a phosphite dehydrogenase protein which is highly soluble in an aqueous solution even in a case where the phosphite dehydrogenase protein is forcibly expressed.

Further, since a temperature of a reaction system rises in industrial production of NADH and NADPH in large quantities, it is necessary to use a phosphite dehydrogenase protein with high thermal stability. However, a conventional wild-type phosphite dehydrogenase protein has low thermal stability (specifically, many enzymes are denatured at 40° C.). As such, there is a demand for a phosphite dehydrogenase protein which can maintain high activity at high temperature.

Under such circumstances, it has been tried to screen for a phosphite dehydrogenase mutant which is improved in the above described properties.

For example, Non-patent Literature 3 discloses a technique in which a phosphite dehydrogenase protein, into which a mutation has been introduced, is forcibly expressed in *E. coli*, so that an amount of a mutated phosphite dehydrogenase protein contained in a soluble fraction is increased. Note that it cannot be determined from the data in Non-patent Literature 3 whether the increase in amount of the mutated phosphite dehydrogenase protein contained in the soluble fraction was caused by an increase in solubility of the mutated phosphite dehydrogenase protein or by an increase in expression level of the mutated phosphite dehydrogenase protein. Further, Non-patent Literatures 4 and 5 disclose mutated phosphite dehydrogenase proteins with high thermal stability.

CITATION LIST

Non-Patent Literatures

Non-Patent Literature 1
Angew. Chem. Int. Ed. 2002, 41, No. 17, 3257-3259
Non-Patent Literature 2
The Journal of Biological Chemistry, Vol. 276, No. 20, Issue of May 18, 2001, 17429-17436
Non-Patent Literature 3
Combinatorial Chemistry and High Throughput Screening, 2006, 9, 237-245
Non-Patent Literature 4
Biotechnology and Bioengineering, Vol. 99, No. 2, Feb. 1, 2008, 268-274
Non-Patent Literature 5
Applied and Environmental Microbiology, October 2005, 5728-5734

SUMMARY OF INVENTION

Technical Problem

However, it was not possible to simultaneously improve both solubility and thermal stability of a conventional mutated phosphite dehydrogenase protein.

The present invention is made in view of the conventional problem. An object of the present invention is to provide a method for producing a phosphite dehydrogenase protein in which both solubility and thermal stability are improved simultaneously, and use of the phosphite dehydrogenase protein.

Solution to Problem

It is difficult to predict how a mutation of amino acid in a protein affects a protein structure. For example, in a case where a mutation that contributes to thermal stability and a mutation that contributes to solubility are both introduced into a single protein, the introduction very often results in cases where (i) the effect of the mutation that contributes to solubility is canceled out by the mutation that contributes to thermal stability, (ii) the effect of the mutation that contributes to thermal stability is canceled out by the mutation that contributes to solubility, or (iii) the mutation that contributes to thermal stability and the mutation that contributes to solubility cancel out each other's effect. That is, a protein having both improved thermal stability and improved solubility cannot always be obtained by the introduction, into a single protein, both of the mutation that contributes to thermal stability and the mutation that contributes to solubility.

In view of this, the inventors have achieved the present invention by use of their own screening method to isolate, from nature, phosphite dehydrogenase having both improved thermal stability and improved solubility.

In order to achieve the object, a protein of the present invention is a protein of the following (a) or (b):

(a) a protein consisting of the amino acid sequence of SEQ ID NO: 1; and (b) a protein (i) consisting of amino acids in which one or several amino acids are deleted, substituted, or added in the amino acid sequence of SEQ ID NO: 1 and (ii) having a phosphite dehydrogenase activity.

This arrangement makes it possible to easily utilize a protein having both improved thermal stability and improved solubility.

Advantageous Effects of Invention

According to the present invention, a phosphite dehydrogenase protein which is highly soluble in an aqueous solution can be obtained in large quantities.

According to the present invention, a phosphite dehydrogenase protein which has high heat resistance can be obtained in large quantities.

According to the present invention, a phosphite dehydrogenase protein which is not inhibited by various inhibitors can be obtained in large quantities.

According to the present invention, a phosphite dehydrogenase protein which has reaction efficiency higher than that of a conventional phosphite dehydrogenase protein can be obtained in large quantities.

DESCRIPTION OF EMBODIMENTS

Figure 1:
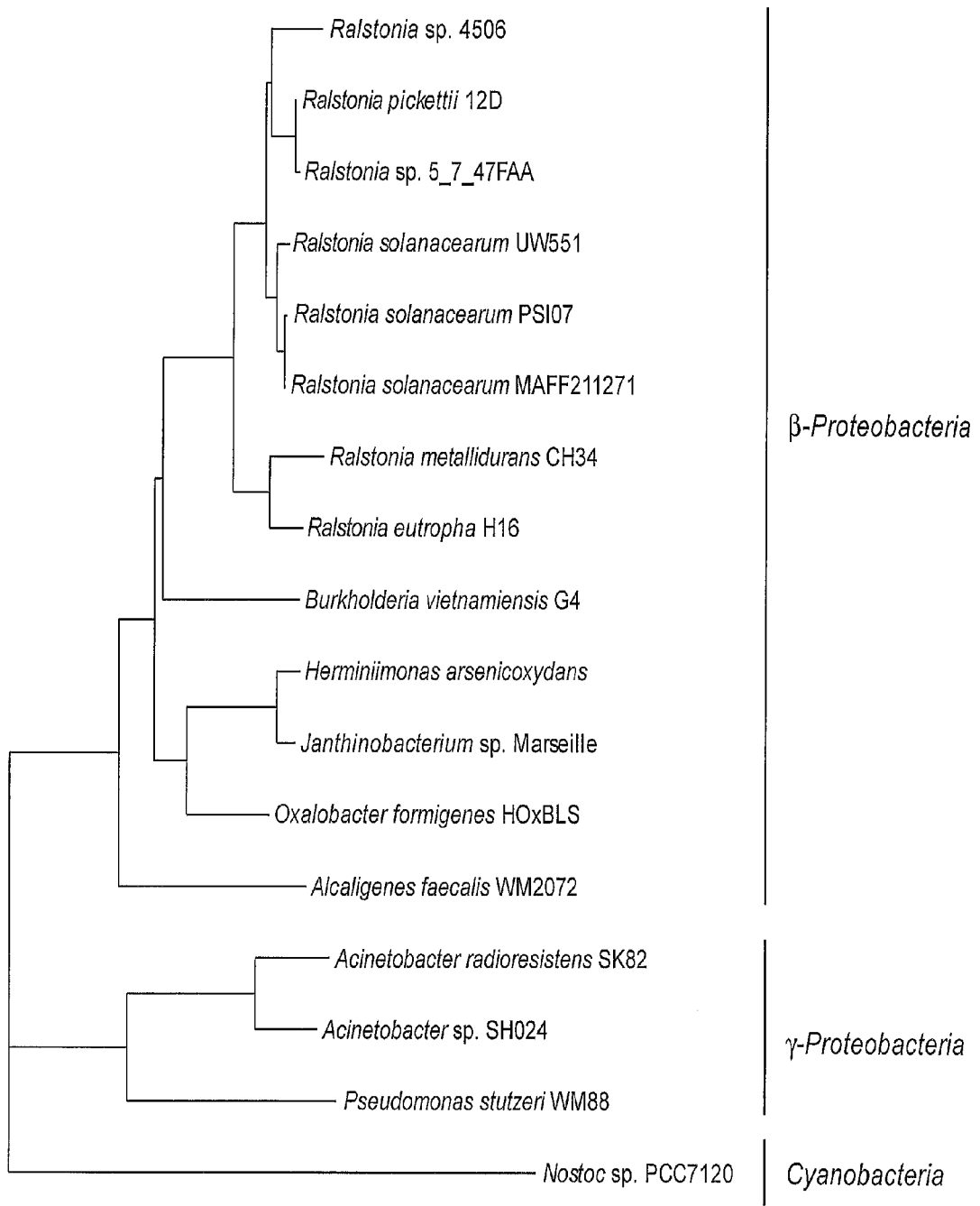
FIG. 1 is a phylogenetic tree of bacteria screened in an example of the present invention.

One embodiment of the present invention is described below. Note, however, that the present invention is not limited to this. As used herein, "A-B" means "not less than A but not more than B."

[1. Protein and Gene]

A protein (phosphite dehydrogenase protein) of the present embodiment is a protein of the following (a) or (b):

(a) a protein consisting of the amino acid sequence of SEQ ID NO: 1; and (b) a protein (i) consisting of amino acids in which one or several amino acids are deleted, substituted, or added in the amino acid sequence of SEQ ID NO: 1 and (ii) having a phosphite dehydrogenase activity.

Details of the "amino acids in which one or several amino acids are deleted, substituted, or added" are described later.

The protein of the present embodiment may be a protein (i) having a homology of not less than 85.0%, preferably not less than 90.0%, more preferably not less than 95.0%, and more preferably not less than 98.0% to the amino acid sequence of SEQ ID NO: 1 and (ii) having a phosphite dehydrogenase activity.

The protein of the present embodiment is a protein having excellent properties: high solubility in an aqueous solution and high heat resistance.

A gene of the present embodiment is a gene encodes the protein of (a) or (b). The gene of the present embodiment may be a gene which is made up of any combination of codons, provided that the gene encodes the protein of (a) and (b).

More specifically, the gene of the present embodiment may be a gene consisting of DNA of the following (c) or (d):

(c) DNA consisting of the base sequence of SEQ ID NO: 2; and (d) DNA that is hybridizable, under a stringent condition, with a complementary base sequence of DNA consisting of the base sequence of SEQ ID NO: 2 and encodes a phosphite dehydrogenase protein.

Details of the "stringent condition" are described later.

[2. Method for Producing Phosphite Dehydrogenase Protein]

A method, of the present embodiment, for producing a phosphite dehydrogenase protein is a production method which includes a step of causing a protein of the following (a) or (b) to be expressed in a host and a step of solubilizing, in a solution, the protein expressed in the host:

(a) a protein consisting of the amino acid sequence of SEQ ID NO: 1; and (b) a protein (i) consisting of amino acids in which one or several amino acids are deleted, substituted, or added in the amino acid sequence of SEQ ID NO: 1 and (ii) having a phosphite dehydrogenase activity.

First, the following description discusses the step of causing the protein of (a) or (b) to be expressed in the host.

The protein consisting of the amino acid sequence of SEQ ID NO: 1 is a phosphite dehydrogenase protein which was obtained by the inventors by screening (see Examples).

The protein expressed in the host may be a protein (i) consisting of amino acids in which one or several amino acids are deleted, substituted, or added in the amino acid sequence of SEQ ID NO: 1 and (ii) having a phosphite dehydrogenase activity. Note, here, that a site at which the one or several amino acids are deleted, substitute, or added is not limited to a specific one and may be any site of the protein, as long as the protein has a phosphite dehydrogenase activity after the one or several amino acids are deleted, substitute, or added. The number of amino acids intended by "one or several amino acids" is not particularly limited, but is preferably not greater than 10, more preferably not greater than 8, and most preferably not greater than 6.

The protein expressed in the host may be a protein (i) having a homology of not less than 85.0%, preferably not less than 90.0%, more preferably not less than 95.0%, and more preferably not less than 98.0% to the amino acid sequence of SEQ ID NO: 1 and (ii) having a phosphite dehydrogenase activity.

Note that a homology of an amino acid sequence can be found by a publicly known method. Specifically, homology search of the amino acid sequence of SEQ ID NO: 1 and a comparative amino acid sequence can be carried out with use of GENETYX-WIN (produced by Genetyx Corporation) in accordance with the manual of GENETYX-WIN, thereby calculating a homology in terms of a proportion (%) of identical amino acid sequences.

The protein expressed in the host may be a fusion protein of (i) the above-described protein and (ii) another protein or a tag. The another protein and the tag are not limited to specific ones, and can be a desired protein (e.g., GST protein or the like) or a tag (e.g., His tag, HA tag, Flag tag, or the like).

As described above, the method, of the present embodiment, for producing a phosphite dehydrogenase protein includes the step of causing the above-described protein to be expressed in the host.

The host is not limited to a specific one, and a desired host can be suitably used. Examples of the host includes, but not limited to, bacteria such as coliforms (e.g., *E. coli* or the like), yeast (e.g., budding yeast *Saccharomyces cerevisiae*, fission yeast *Schizosaccharomyces pombe*, or the like), an insect cell, a nematode (e.g., *Caenorhabditis elegans* or the like), an oocyte of *Xenopus laevis* or the like, a mammalian cell (e.g., CHO cell, COS cell, and Bowes melanoma cell), a human cultured cell of any kind, and the like.

The step of causing the above-described protein to be expressed in the host is not limited to a specific arrangement, as long as it is a step that allows the protein of the (a) or (b) to be expressed in the host. For example, the step of causing the above-described protein to be expressed in the host may include a step of introducing, into the host, a vector including DNA consisting of a base sequence encoding the protein of (a) or (b). A specific base sequence of DNA is not particularly limited, and a codon sequence of any kind can be used for each amino acid in the protein. DNA may be, for example, DNA of the following (c) or (d):

(c) DNA consisting of the base sequence of SEQ ID NO: 2; and (d) DNA that is hybridizable, under a stringent condition, with a complementary base sequence of DNA consisting of the base sequence of SEQ ID NO: 2 and encodes a phosphite dehydrogenase protein.

DNA consisting of the base sequence of SEQ ID NO: 2 is a phosphite dehydrogenase gene which was obtained by the inventors by screening, and is DNA which encodes the protein consisting of the amino acids of SEQ ID NO: 1.

DNA included in the vector may be DNA that is hybridizable, under a stringent condition, with a complementary base sequence of DNA consisting of the base sequence of SEQ ID NO: 2 and encodes a phosphite dehydrogenase protein.

As used herein, the term "stringent condition" means overnight incubation at 42° C. in a hybridization solution (50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured sheared salmon sperm DNA), followed by washing the filters in 0.1× SSC at about 65° C. High stringency wash conditions are adjusted appropriately in accordance with a polynucleotide to be hybridized. For example, in a case where DNA derived from a mammal is used, the filters are preferably washed in 0.5×SSC containing 0.1% SDS at 65° C. (preferably 15 min.×2 times). In a case where DNA derived from *E. coli* is used, the filters are preferably washed in 0.1×SSC containing 0.1% SDS at 68° C. (preferably 15 min.×2 times). In a case where RNA is used, the filters are preferably washed in 0.1× SSC containing 0.1% SDS at 68° C. (preferably 15 min.×2 times). In a case where an oligonucleotide is used, the filters are preferably washed in 0.1×SSC containing 0.1% SDS at a hybridization temperature (preferably 15 min.×2 times). The hybridization can be carried out in accordance with a well-known method described in Sambrook et al.: Molecular Cloning, A Laboratory Manual, 2d Ed., Cold Spring Harbor Laboratory (1989).

The vector including DNA consisting of the base sequence encoding the protein of (a) or (b) is not limited to a specific one, and can be suitably selected in accordance with the host. The vector can include an expression regulatory region (e.g., a promoter, a terminator, an origin of replication, and/or the like) depending on the host to be introduced. Examples of the promoter encompass a viral promoter (e.g., an SV40 early promoter, an SV40 late promoter, or the like) and the like. Further, the promoter may be an expression-inducible promoter whose expression can be induced with use of IPTG or the like.

The vector preferably includes at least one selection marker. Examples of such a marker encompass ampicillin, dihydrofolate reductase, a neomycin resistance gene, and the like. Use of the selection marker not only allows checking whether or not the vector has been introduced into the host, but also allows checking whether or not a desired protein is certainly expressed in the host.

A method for introducing the vector to the host is not limited to a specific one, and a well-known method can be used appropriately. For example, a conventionally known method such as electroporation, a calcium phosphate method, a liposome method, a DEAE dextran method, or the like can be suitably used. More specifically, in a case where the vector is introduced into a host microorganism belonging to the genus *Escherichia*, it is possible to apply a method in which recombinant DNA is introduced in the presence of calcium ions, or a method in which electroporation is used.

Next, the following description will discuss the step of solubilizing the protein expressed in the host.

The step of solubilizing the protein expressed in the host may include a step of disrupting the host, in which the protein is expressed, into fragments in a solution. The step of solubilizing the protein expressed in the host may further include a step of centrifuging the fragments, in addition to the step of disrupting the host, in which the protein is expressed, into the fragments in the solution. This arrangement allows a large amount of the protein to be solubilized in the solution. This makes it possible to purify a desired protein in large quantities and in high purity.

The solution for disrupting the host is not limited to a particular one, and may be, for example, a surfactant (e.g., Tween-20 (Registered Trademark), Triton-X100 (Registered Trademark), SDS, or the like), NaCl, or a solution containing both the surfactant and NaCl.

A concentration of the surfactant in the solution is not particularly limited, but is, for example, preferably not less than 0 (w/v) but not more than 1.0% (w/v), more preferably not less than 0 (w/v) but not more than 0.5% (w/v), more preferably not less than 0 (w/v) but not more than 0.3% (w/v), more preferably not less than 0 (w/v) but not more than 0.1% (w/v), and most preferably not less than 0 (w/v) but not more than 0.01% (w/v). Note that a lower limit of each of the above numerical ranges may be 0.01% (w/v) or 0.001% (w/v). In the present embodiment, the protein expressed in the host is originally highly soluble in a solution. Accordingly, the protein can be solubilized in a solution sufficiently even in a case where a low-concentration surfactant is used.

A surfactant is likely to inhibit various chemical reactions. For example, in production of NADH or NADPH with use of a phosphite dehydrogenase protein, the presence of a surfactant is likely to inhibit a chemical reaction. According to the method of the present embodiment for producing a phosphite dehydrogenase protein, the concentration of the surfactant for solubilizing the phosphite dehydrogenase protein may be low. This allows minimizing an amount of the surfactant mixed in the produced phosphite dehydrogenase protein. As a result, in production of NADH, NADPH, or the like with use of the produced phosphite dehydrogenase protein, NADH or NADPH can be efficiently produced in large quantities.

A concentration of NaCl in the solution is not particularly limited, but is, for example, preferably not less than 0 mM but not more than 150 mM, more preferably not less than 0 mM but not more than 100 mM, more preferably not less than 0 mM but not more than 50 mM, more preferably not less than 0 mM but not more than 40 mM, more preferably not less than 0 mM but not more than 20 mM, more preferably not less than 0 mM but not more than 10 mM, and most preferably 0 mM. Note that a lower limit of each of the above numerical ranges may be 0.01 mM or 0.001 mM. In the present embodiment, the protein expressed in the host is originally highly soluble in a solution. Accordingly, the protein can be solubilized in a solution sufficiently even in a case where low-concentration NaCl is used.

As described later in Examples, NaCl has the effect of inhibiting an activity of a phosphite dehydrogenase protein. It is therefore preferable to solubilize a phosphite dehydrogenase protein in a solution in which the concentration of NaCl is reduced as much as possible. In order to solubilize a conventional phosphite dehydrogenase protein, high-concentration NaCl was used in addition to a surfactant, since conventional phosphite dehydrogenase had low solubility. On the other hand, according to the method of the present embodiment for producing a phosphite dehydrogenase protein, the concentration of NaCl for solubilizing the phosphite dehydrogenase protein may be low. This allows minimizing an amount of NaCl mixed in the produced phosphite dehydrogenase protein. As a result, in production of NADH, NADPH, or the like with use of the produced phosphite dehydrogenase protein, NADH or NADPH can be efficiently produced in large quantities.

A pH of the solution can be adjusted with use of a publicly known buffer. The buffer is not limited to a specific one, and can be any buffer that has a sufficient buffering ability in a pH range of 6.0 to 8.5. Examples of the buffer in the pH range encompass phosphate, Tris, bis-tris propane, N-tris(hydroxymethyl)methyl-2-aminoethanesulfonic acid (TES), 2-(N-morpholino)ethanesulfonic acid monohydrate (MES), piperazine-1,4-bis(2-ethanesulfonic acid) (PIPES), 2-[4-(2-Hydroxyethyl)-1-piperazinyl]ethanesulfonic acid (HEPES), 3-[N-tris(hydroxymethyl)methylamino]-2-hydroxypropanesulfonic acid (TAPSO), and the like. A concentration of the buffer in the solution is not particularly limited, but may be, for example, 20 mM to 200 mM.

The method of the present embodiment for producing a phosphite dehydrogenase protein can include a step of heating the host in which the protein is expressed or the fragments of the host in which the protein is expressed. As described later in Examples, the phosphite dehydrogenase protein of the present embodiment has high heat resistance. As such, the step of heating makes it possible to denature unnecessary enzymes without denaturing phosphite dehydrogenase. That is, the step of heating makes it possible to prevent an activity of an unnecessary enzyme from being mixed in phosphite dehydrogenase obtained by the method of the present embodiment for producing a phosphite dehydrogenase protein.

Although a specific method for carrying out the step for heating is not particularly limited, it is possible, for example, to (i) heat a culture solution including the host in which the protein is expressed, (ii) separate, from a culture solution, the host in which the protein is expressed and then heat the host, or (iii) separate, from a culture solution, the host in which the protein is expressed, subsequently disrupt the host into fragments, and then heat the fragments.

In the step of heating, the host in which the protein is expressed or the fragments of the host in which the protein is expressed is/are preferably heated to 35° C. to 55° C., more preferably heated to 40° C. to 52.5° C., further more preferably heated to a temperature in a range of 40° C. to 50° C., and most preferably heated to a temperature in a range of 40° C. to 45° C.

Time during which the heating is performed is not particularly limited, but is preferably, for example, 0 minute to 60 minutes, more preferably 15 minutes to 30 minutes.

In the step of heating, it is preferable that the phosphite dehydrogenase protein which is expressed and a protease inhibitor are both present. According to this arrangement, even in a case where protease is present, the phosphite dehydrogenase protein can be prevented from being decomposed by protease.

The protease inhibitor is not particularly limited, and a publicly known protease inhibitor can be appropriately used. Examples of the protease inhibitor encompass a low-molecular-weight inhibitor (e.g., diisopropylfluorophosphate, phenylmethanesulfonyl fluoride, p-mercuribenzoic acid, iodoacetic acid, diazoacetyl-DL-norleucine methyl ester, phosphoramide, or the like), an inhibitor peptide (e.g., leupeptin, antipain, chymostatin, pepstatin, or the like), an inhibitor protein (e.g., alpha2-macroglobulin, calpastatin, or the like), but are not limited to these.

[3. Method for Producing NADH or NADPH]

A method, of the present embodiment, for producing NADH is a method in which a phosphite dehydrogenase protein produced by the method, of the present invention, for producing a phosphite dehydrogenase protein is used as an enzyme so as to cause $HPO_3^{2-}$, $NAD^+$, and $H_2O$ to react with one another. For a specific reaction formula, see (Reaction formula 1) in the section [Background Art].

The method, of the present embodiment, for producing NADPH is a method in which a phosphite dehydrogenase protein produced by the method of the present invention for producing a phosphite dehydrogenase protein is used as an enzyme so as to cause $HPO_3^{2-}$, $NADP^+$, and $H_2O$ to react with each other. For a specific reaction formula, see (Reaction formula 2) in the section [Background Art].

A temperature at which the reaction is carried out is not particularly limited, but is, for example, preferably 35° C. to 55° C., more preferably 40° C. to 52.5° C., further more preferably 40° C. to 50° C., and most preferably 40° C. to 45° C. As described later in Examples, an optimal temperature of a phosphite dehydrogenase protein produced by the method of the present invention for producing a phosphite dehydrogenase protein is very high as compared with conventional phosphite dehydrogenase. As such, the above arrangement allows efficient mass-production of NADH or NADPH. Further, according to the arrangement, a reaction temperature is high. Accordingly, even in a case where an unnecessary enzyme is mixed in a reaction system, it is possible to denature only the unnecessary enzyme mixed in.

To adjust the reaction system to the above-mentioned temperature, temperature adjustment may be carried out by applying heat to the reaction system from outside, or by using reaction heat which is generated as a chemical reaction progresses. That is, use of the phosphite dehydrogenase protein produced by the method of the present invention for producing a phosphite dehydrogenase protein has an advantage of not having to cool the reaction system.

The reaction can be performed in the presence of arsenite, nitrate, sulfate, or NaCl. As described later in Examples, an activity of conventional phosphite dehydrogenase is significantly decreased by the presence of arsenite, nitrate, sulfate, or NaCl. On the other hand, the presence of arsenite, nitrate, sulfate, or NaCl does not cause a significant decrease in activity of the phosphite dehydrogenase protein produced by the method of the present invention for producing a phosphite dehydrogenase protein. Accordingly, the method of the present embodiment for producing NADH or NADPH allows efficient production of NADH or NADPH even in the presence of arsenite, nitrate, sulfate, or NaCl.

A concentration of arsenite, nitrate, sulfate, or NaCl in the reaction system is not particularly limited. For example, the concentration is preferably not more than 100 mM, more preferably not more than 70 mM, more preferably not more than 50 mM, and most preferably not more than 40 mM, but is not limited to these. A lower limit of the concentration is not particularly limited, but may be 0.1 mM, 0.01 mM, or 0 mM.

[4. Kit for Manufacturing NADH or NADPH]

A kit of the present embodiment is a kit for producing NADH or NADPH.

The kit of the present embodiment may include a protein produced by the method of the present invention for producing a phosphite dehydrogenase protein. Further, the kit of the present embodiment may include a vector for causing a phosphite dehydrogenase protein of the present invention to be expressed in a desired host. Since the details of these arrangements have already been described, description on such details is omitted in the following description.

A gene of the present invention is a gene which encodes a protein of the present invention.

The gene of the present invention may be a gene consisting of DNA of the following (c) or (d):

(c) DNA consisting of the base sequence of SEQ ID NO: 2; and (d) DNA that is hybridizable, under a stringent condition, with a complementary base sequence of DNA consisting of the base sequence of SEQ ID NO: 2, and encodes a phosphite dehydrogenase protein.

The method of the present invention for producing a phosphite dehydrogenase protein may include (i) a step of causing a protein of the present invention to be expressed in a host and (ii) a step of solubilizing, in a solution, the protein expressed in the host.

In the method of the present invention for producing a phosphite dehydrogenase protein, the step of causing the protein of the present invention to be expressed may include a step of introducing, into the host, a vector including the gene of the present invention.

In the method of the present invention for producing a phosphite dehydrogenase protein, the step of solubilizing the protein expressed in the host may include a step of disrupting the host, in which the protein is expressed, in a solution containing at least one of (i) not less than 0 (w/v) but not more than 0.1% (w/v) of a surfactant and (ii) not less than 0 (w/v) but not more than 50 mM of NaCl.

In the method of the present invention for producing a phosphite dehydrogenase protein, the surfactant may be Tween-20 or Triton-X100.

The method of the present invention for producing a phosphite dehydrogenase protein may include a step of heating (i) the host in which the protein is expressed or (ii) the fragments of the host in which the protein is expressed.

In the method of the present invention for producing a phosphite dehydrogenase protein, the step of heating may be a step of heating, to a temperature in a range of 40° C. to 50° C., the host in which the protein is expressed or the fragments of the host in which the protein is expressed.

In the method of the present invention for producing NADH or NADPH, the protein of the subject application or the phosphite dehydrogenase protein produced by the method of the present invention for producing a phosphite dehydrogenase protein is used as an enzyme so as to react $NAD^+$ or $NADP^+$ with $HPO_3^{2-}$ and $H_2O$.

In the method of the present invention for producing NADH or NADPH, the reaction may be carried out at a temperature in a range of 40° C. to 50° C.

In the method of the present invention for producing NADH or NADPH, the reaction may be carried out in the presence of arsenite, nitrate, sulfate, or NaCl.

EXAMPLES

1. Screening of Phosphite Dehydrogenase Based on Heat Resistance

Microorganisms which were capable of growing in a 45° C. environment and producing NADH in a phosphorous acid-dependent manner were screened. Details of the screening were as follow.

Collected soil was dissolved in sterile water. 0.4 mL of a solution thus obtained was added to 3.6 mL of a MOPS liquid culture medium (0.5 mM phosphite, 22.2 mM glucose, 40 mM potassium morpholinopropane sulfonate [pH 7.2], 50 mM NaCl, 9.52 mM $NH_4Cl$, 4 mM Tricine, 2 mM $K_2HPO_4$, 0.52 mM $MgCl_2$, 0.28 mM $K_2SO_4$, 0.01 mM $FeSO_4$, 0.0005 mM $CaCl_2$, and 20 μM thiamine) containing 0.5 mM phosphorous acid, and was incubated for 7 days at 45° C. for enrichment culturing.

After the 7-day enrichment culturing, a culture obtained was inoculated on (i) a MOPS agar medium (0.5 mM phosphite, 22.2 mM glucose, 40 mM potassium morpholinopropane sulfonate [pH7.2], 50 mM NaCl, 9.52 mM $NH_4Cl$, 4 mM Tricine, 2 mM $K_2HPO_4$, 0.52 mM $MgCl_2$, 0.28 mM $K_2SO_4$, 0.01 mM $FeSO_4$, 0.0005 mM $CaCl_2$, 20 μM thiamine, and 1.5% Agar) containing 0.5 mM phosphorous acid, (ii) a MOPS agar medium containing 2 mM phosphoric acid, and (iii) a MOPS agar medium containing no phosphorous acid or phosphoric acid, and was incubated for 1 to 3 days at 45° C. Then, a plurality of colonies of microorganisms which had appeared on the MOPS agar medium containing 0.5 mM phosphorous acid were isolated.

The microorganisms which formed each of the colonies were incubated with use of a MOPS liquid culture medium containing 0.5 mM phosphorous acid to examine whether or not the microorganisms had a phosphite dehydrogenase activity.

The following description will explain how the phosphite dehydrogenase activity was measured.

The microorganisms of each of the colonies, which had been preserved in a frozen state in a glycerol solution, were inoculated on 4 mL of a 2×YT liquid culture medium, and were incubated overnight at 45° C. 1 mL of a culture solution thus obtained was charged into a 1.5-mL tube, and then the tube was centrifuged at 12000 rpm for 5 minutes. Then, a supernatant was discarded to obtain a pellet of bacteria.

In order to remove phosphoric acid derived from the culture medium, the pellet of the bacteria was suspended in 1 mL of a MOPS (0) solution (a MOPS culture medium which contains no phosphorus component), and a suspension thus obtained was centrifuged at 12000 rpm for 5 minutes. Then, a supernatant was discarded to obtain a pellet of bacteria. This washing operation was repeated once to obtain a pellet of bacteria, which was then suspended in 1 mL of a MOPS (0) solution. Subsequently, 100 μL of a suspension thus obtained was inoculated on 10 mL of a MOPS-phosphorous acid (0.5 mM) liquid culture medium, and was cultivated at 45° C.

When a value of $OD_{600}$ reached 1.5 to 2.0 after 24 to 72 hours of culture, a whole of the culture medium was transferred to a 50-mL tube, and then the tube was centrifuged at 6000 rpm for 10 minutes. After the centrifugation, a supernatant was discarded to obtain a pellet of bacteria.

The pellet of the bacteria was suspended in 10 mL of a MOPS (0) solution, and then subjected to ultrasonic disruption (Digital sonifier, BRANSON) for 10 minutes with a 20% output. The MOPS (0) solution having been subjected to the ultrasonic disruption was dispensed to an ultracentrifugation tube (Centrifuge Tubes, BECKMAN, 349622), and the ultracentrifugation tube was ultracentrifuged in an ultracentrifuge (Optima™ TLX Ultracentrifuge, BECKMAN COULTER) at 270,000×g and 4° C. for 45 minutes.

After the ultracentrifugation, a supernatant was collected to be used as a crude extract for measuring phosphite dehydrogenase activity. A total of 1000 μL of a reaction solution was prepared which contained the crude extract (protein amount: 10 μg), $NAD^+$ (1 mM), phosphorous acid (1 mM), and a MOPS-KOH buffer (20 mM, pH 7.4). A temperature of the reaction solution was elevated to 45° C., so that a reaction was started. A sample was collected, each in an amount of 100 μL, at predetermined time intervals for a predetermined period of time (0 to 180 minutes), and absorbance (340 nm) of each sample was measured. Phosphite dehydrogenase activity was evaluated in terms of an amount of NADH generated by 1 mg of protein per unit time.

In this way, microorganisms which were capable of growing under a 45° C. condition and producing NADH in a phosphorous acid-dependent manner were screened. The number of strains of the screened microorganisms was 5.

2. Classification of Screened Microorganisms and Acquisition of Phosphite Dehydrogenase Gene The five strains had almost identical phosphite dehydrogenase activities in the crude extract, and were morphologically and physiologically similar to one another. It was therefore considered that all the five strains were closely related bacteria. In view of this, a strain (strain #4506) which had proliferated the most among the 5 strains were used in subsequent analyses.

First, strain #4506 was classified based on a base sequence of 16S rRNA (16S ribosomal RNA), and the base sequence of a phosphite dehydrogenase gene of each strain was determined. A specific method for the determination is described below in detail.

In accordance with the literature: J. R. Marchesi, et al., Applied and Environmental Microbiology, 64, p. 795-799 (1998), chromosomal DNA was extracted from strain #4506 obtained by the screening, and a 16s rRNA gene was amplified with use of the chromosomal DNA.

First, the 16S rRNA gene was amplified by PCR. In the PCR, a primer 1 and a primer 2 (shown below) were used as primers, and a KOD-plus produced by Toyobo Co., Ltd. was used to carry out a PCR reaction. Specific conditions for the PCR reaction were as follows. A temperature of a reaction solution was maintained at 72° C. for 5 minutes. Subsequently, a reaction cycle, which was made up of a denaturation step at 95° C. for 1 minute, an annealing step at 55° C. for 1 minute, and an extension step at 72° C. for 1.5 minutes, was cycled 30 times.

```
Primer 1:
5'-AGAGTTTGATCCTGGCTCAG-3'    (SEQ ID NO: 5)

Primer 2:
5'-GTCCCGCAACGAGCGCAAC-3'     (SEQ ID NO: 6)
```

A base sequence of 16S rRNA thus amplified was determined with use of a DYEnamic ET Terminator (produced by Applied Biosystems). Specific procedures of the determination were based on protocols attached to the DYEnamic ET Terminator.

The determined base sequence of 16S rRNA was analyzed with use of Clustal W2, which is a phylogenetic tree creation tool, so that strain #4506 was classified. Specific procedures of the analysis were based on protocols attached to Clustal W2.

FIG. 1 shows a phylogenetic tree of strain #4506 screened. From this result, it became clear that strain #4506 was a bacterium belonging to the genus *Ralstonia*. In connection with this, strain #4506 was named *Ralstonia* sp. strain 4506.

"*Ralstonia* sp. 4506" shown in FIG. 1 corresponds to strain #4506 which was screened. "*Ralstonia* sp. 5_7_47FAA," "*Ralstonia* metallidurans CH34," "*Alcaligenes faecalis* WN2072," and "*Pseudomonas stutzeri* WM88" were well-known strains. A phosphite dehydrogenase gene and a phosphite dehydrogenase protein of these strains were also well known, or the presence of the phosphite dehydrogenase gene and the phosphite dehydrogenase protein of the strains had been predicted.

"*Ralstonia* sp. 5_7_47FAA" was taxonomically closely related to strain #4506, and the presence of a phosphite dehydrogenase gene of "*Ralstonia* sp. 5_7_47FAA" had been predicted. However, it had not been proved whether or not a protein encoded by the phosphite dehydrogenase gene actually had a phosphite dehydrogenase activity. Further, a base sequence on the 3'-terminal side of the phosphite dehydrogenase gene (i.e., an amino acid sequence on the C-terminal side of the phosphite dehydrogenase protein) was unknown (see, for example, "http://www.ncbi.nlm.nih.gov/nuccore/308920199"). As a matter of course, various properties (e.g., solubility, thermal stability, etc.) of the phosphite dehydrogenase protein encoded by the presumed phosphite dehydrogenase gene of "5747FAA" had not been analyzed at all.

Since strain #4506 had grown at 45° C. in the screening, it was predicted that phosphite dehydrogenase included in strain #4506 had heat resistance. Accordingly, screening of the phosphite dehydrogenase gene was tried with strain #4506.

A phosphite dehydrogenase gene (ptxD) of strain #4506 was expected to be different from known ones. As such, a full-length sequence of the phosphite dehydrogenase gene was obtained by (i) obtaining an internal region of the phosphite dehydrogenase gene of strain #4506 by PCR with use of primers designed on the basis of a highly conserved region of a well-known phosphite dehydrogenase gene and (ii) obtaining a 5' region and a 3' region of the phosphite dehydrogenase gene of strain #4506 by inverse PCR. A specific method for this is described below in detail.

First, degenerate primers (PTXD1 and PTXD2) were prepared based on amino acid sequences at two sites (a site from the 76th to the 82nd, and a site from the 261st to the 267th of P stutzeri WM88) which were highly conserved in well-known ptxD. Base sequences of the respective degenerate primers are shown below.

```
PTXD1:
5'-AARGGNTAYGAYAAYTTYGAY-3'   (SEQ ID NO: 7)

PTXD2:
5'-RTCYTCCATYTCRTANACRTC-3'   (SEQ ID NO: 8)
```

PCR was carried out with use of chromosomes of strain #4506, which served as a template, and the degenerate primers. As a result, an amplified DNA fragment of about 600 bp was obtained.

The amplified DNA fragment was cloned to a pGEM T-easy vector (Promega) so as to obtain an amplified DNA fragment, and a base sequence of the amplified DNA fragment was determined. Based on the determined base sequence, it was confirmed that the amplified DNA fragment was an internal sequence of ptxD.

On the basis of the determined base sequence, primers (PTXD3 and PTXD4) for inverse PCR were prepared. Base sequences of the respective primers are shown below.

```
PTXD3:
                              (SEQ ID NO: 9)
5'-TCGTGGATGAGAATGCGGTGATAGC-3'

PTXD4:
                              (SEQ ID NO: 10)
5'-ATAGTCAGTTCAGCGGTCGGGATCG-3'
```

A template used in the inverse PCR was obtained by the following manner. 0.5 µg of chromosomes of strain #4506 were digested for 12 hours with use of 0.5 µL of a restriction enzyme Pst I. Then, the chromosomes were self-ligated with use of T4 DNA ligase, and were further purified. The chromosomes thus purified were used in an amount of 20% relative to a total volume of a reaction solution for the inverse PCR. By carrying out the inverse PCR with use of PTXD3 and PTXD4, approximately 2.5 kb of a DNA fragment was obtained.

The DNA fragment was cloned to a pGEM T-easy vector. Then, base sequences at the respective both terminal sides of the DNA fragment were determined, and a 5' region and a 3' region of ptxD were determined. Based on these sequences, primers (PTXD5 and PTXD6) for obtaining a full-length sequence of ptxD were prepared. Base sequences of the respective primers are shown below.

```
PTXD5:
                              (SEQ ID NO: 11)
5'-CGGGATCCGATGAAGCCCAAAGTCGTCCTC-3'

PTXD6:
                              (SEQ ID NO: 12)
5'-CGGAATTCGCCGCCTTTACTCCCGGATAC-3'
```

With use of PTXD5 and PTXD6, PCR was carried out by using, as a template, chromosomes of strain #4506, thereby amplifying approximately 1 kb of a DNA fragment. A base sequence of the amplified DNA fragment was determined in the same manner as described above.

A base sequence of the phosphite dehydrogenase gene is shown in SEQ ID NO: 2. Further, an amino acid sequence of a phosphite dehydrogenase protein encoded by the phosphite dehydrogenase gene is shown in SEQ ID NO: 1. Note that the base sequence shown in "http://www.ncbi.nlm.nih.gov/nuccore/308920199" mentioned above completely matched a partial sequence of the base sequence of SEQ ID NO: 1.

3. Expression of Phosphite Dehydrogenase Protein By Using *Escherichia Coli*

By a well-known method, the base sequence of SEQ ID NO: 2 or a phosphite dehydrogenase gene (SEQ ID NO: 4) of P stutzeri WM88 was inserted into a plasmid pET21b (produced by Novagen) (an amino acid sequence of the protein encoded by the base sequence of SEQ ID NO: 4 is shown in SEQ ID NO: 3) to prepare (i) an expression vector of a fusion protein (see "PtxD$_{4506}$" in FIG. 2) in which the C-terminal of the phosphite dehydrogenase protein of SEQ ID NO: 1 is labeled with a His tag or (ii) an expression vector of a fusion protein (see "PtxD$_{Pst}$" in FIG. 2) in which the C-terminal of the phosphite dehydrogenase protein of P stutzeri WM88 is labeled with a His tag.

A competent cell Rosetta2 (DE3) (produced by Novagen) was transformed by a well-known method with use of each of the expression vectors.

Transformants thus obtained were inoculated on a 200 mL LB culture medium (containing 10 g of polypeptone, 5 g of yeast extract, and 5 g of NaCl per liter of the culture-medium), and were cultured at 37° C. until OD$_{600}$ reached 0.5. Subsequently, IPTG (isopropyl thiogalactoside) was added to the culture so as to have a concentration of 1 mM. Then, the culture was incubated for another 3 more hours at 28° C.

The culture was centrifuged at 6,000 rpm for 15 minutes, and bacteria, which were sediment, were collected. The bacteria were suspended in a buffer for disruption (50 mM Tris-HCl (pH: 7.4), 50 mM NaCl), and a suspension thus obtained was subjected to an ultrasonic treatment, so that the bacteria were disrupted. Subsequently, Tween20 (Registered Trademark) was added to a resultant solution of the disrupted bacteria so as to have a final concentration of 0.1%, and was left still on ice for 15 minutes. Note that the buffer for disruption containing the disrupted bacteria is indicated as "T" in FIG. 2.

Figure 2:
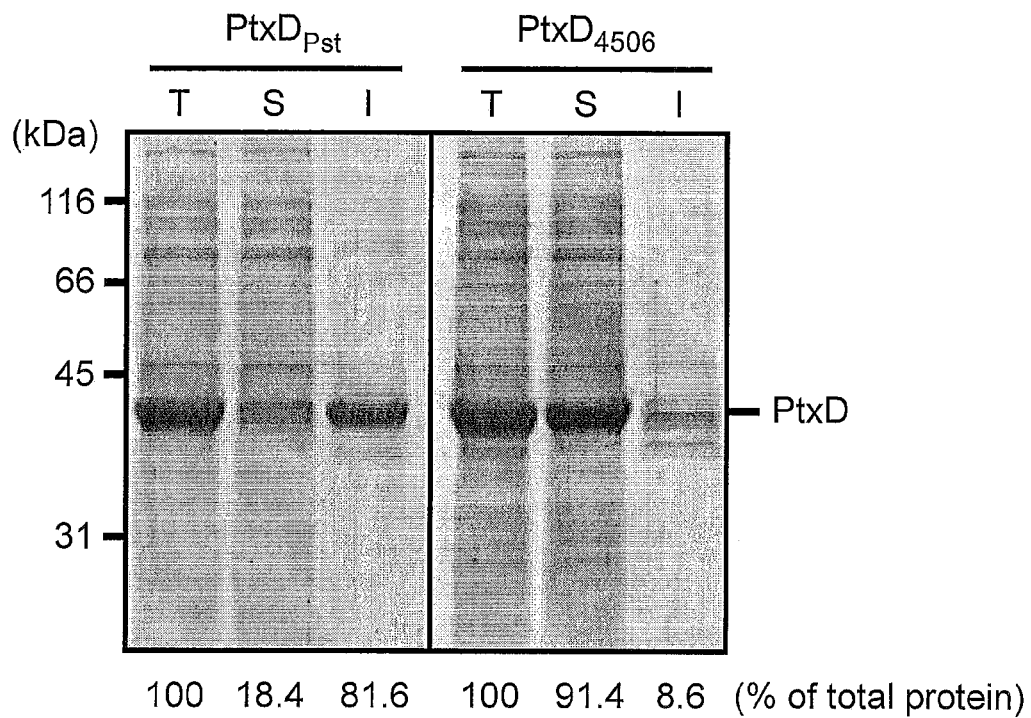
FIG. 2 is a photograph of SDS-PAGE showing a location at which a phosphite dehydrogenase protein of the present invention is present in a case where the phosphite dehydrogenase protein is forcibly expressed in *E. coli*.

The buffer for disruption containing the disrupted bacteria was centrifuged at 15,000 rpm and 4° C. for 15 minutes. After the centrifugation, a resultant product was divided into a supernatant and sediment. In FIG. 2, the supernatant is indicated as "S" and the sediment is indicated as "I."

The supernatant was supplied to a HisTrap column (produced by GE Healthcare) and, in accordance with protocols attached to the HisTrap column, a fusion protein in which a His tag was connected to the C-terminal of the phosphite dehydrogenase protein of SEQ ID NO: 1 was purified.

The buffer for disruption (T) containing the disrupted bacteria, the supernatant (S), and the sediment (I) described above were separated by SDS-PAGE. Subsequently, an acrylamide gel was dyed with CBB stain one (produced by Nacalai), and an amount of the phosphite dehydrogenase protein was measured.

The measurement results are shown in FIG. 2.

In the case of the fusion protein in which the His tag was connected to the C-terminal of the phosphite dehydrogenase protein of P stutzeri WM88, approximately 18.4% of the fusion protein was present in the supernatant (S), and approximately 81.6% of the fusion protein was present in the sediment (I). On the other hand, in the case of the fusion protein in which the His tag was connected to the C-terminal of the phosphite dehydrogenase protein of SEQ ID NO: 1, approximately 91.4% of the fusion protein was present in the supernatant (S), and approximately 8.6% of the fusion protein was present in the sediment (I). From the results, it became clear that the fusion protein in which the His tag was connected to the C-terminal of the phosphite dehydrogenase protein of SEQ ID NO: 1 had a dramatically improved solubility.

4. Heat Resistance of Phosphite Dehydrogenase Protein $PtxD_{4506}$ and $PtxD_{Pst}$, which were purified with use of the HisTrap column in [3. Expression of Phosphite Dehydrogenase Protein Using *Escherichia Coli*] were examined in terms of heat resistance. The following description discusses how measurement of heat resistance was carried out.

Each of the purified $PtxD_{4506}$ and $PtxD_{Pst}$ was added to 50 mM of a MOPS buffer (pH 7.4) so as to have a final concentration of 0.2 mg/mL. 100 μL of an enzyme solution thus obtained was supplied to a 1.5-mL tube, and 100 μL of mineral oil was added to the enzyme solution in order to prevent evaporation. A temperature of the tube was maintained at 10° C. to 60° C. for 12 hours. The enzyme solution was sampled in an amount of 10 μL (2 μg) over time, and 490 μL of 20 mM MOPS-KOH buffer (pH 7.4) containing 1 mM $NAD^+$ and 1 mM phosphorous acid was added to the sampled enzyme solution to obtain a total of 500 μL of a reaction system. The measurement of phosphite dehydrogenase activity was carried out with the reaction system.

Figure 3:
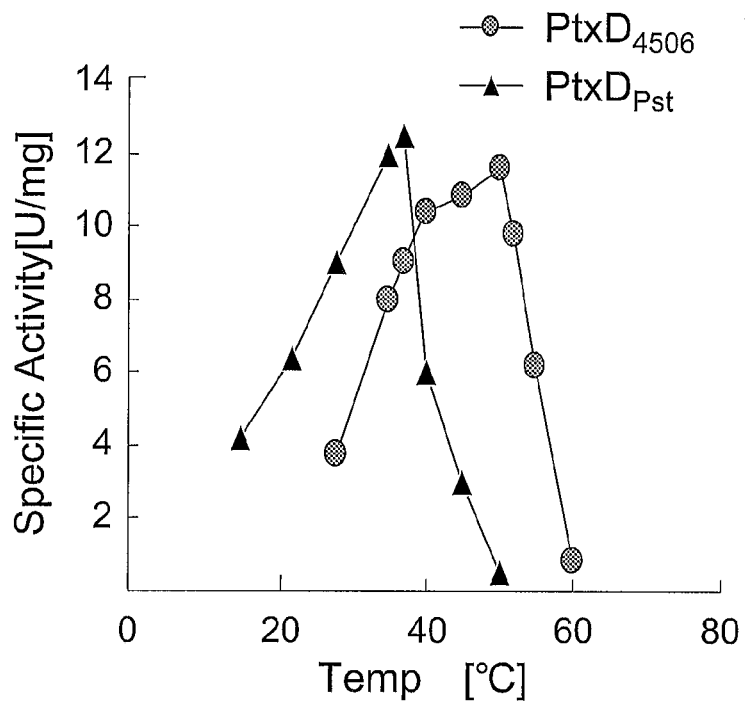
FIG. 3 is a graph showing heat resistance of a phosphite dehydrogenase protein of the present invention.

The measurement results are shown in FIG. 3.

As shown in FIG. 3, it became clear that $PtxD_{Pst}$ has a specific activity which is the highest at about 35° C. and rapidly decreases both below and above 35° C. That is, it became clear that $PtxD_{Pst}$ has a low optimum temperature (about 35° C.) and a very narrow range of a temperature suitable for reaction.

On the other hand, it became clear that $PtxD_{4506}$ has a specific activity which is the highest at about 50° C. and can be maintained high in a broad range of temperatures both below and above 50° C. Specifically, it became clear that an average specific activity of $PtxD_{4506}$ is high at a temperature in a range of 35° C. to 55° C., particularly high at a temperature in a range of 40° C. to 52.5° C., and even more particularly high at a temperature in a range of 40° C. to 50° C. This shows that the fusion protein $PtxD_{4506}$ is capable of stably producing a large amount of substance even in a production process of a substance whose temperature is easily elevated (e.g., NADH or NADPH production process). This shows that an activity of phosphite dehydrogenase is not lost even in a case where phosphite dehydrogenase is heated in a production process of a phosphite dehydrogenase protein.

5. Reaction Kinetic Analysis of Phosphite Dehydrogenase Protein $PtxD_{4506}$ and $PtxD_{Pst}$, which were purified with use of the HisTrap column in [3. Expression of Phosphite Dehydrogenase Protein By Using *Escherichia Coli*], were compared with each other in terms of reaction rate. The following description discusses how measurement of reaction rates was carried out.

Reaction rates of respective $PtxD_{4506}$ and $PtxD_{Pst}$ were calculated on the basis of (Reaction formula 1) shown in the section [Background Art].

Specifically, in the reaction system of (Reaction formula 1), a production rate of NADH was measured with use of 7.5 μg of each of the fusion proteins $PtxD_{4506}$ and $PtxD_{Pst}$ while a concentration of a substrate ($NAD^+$) was gradually changed from 0.5 μM to 200 μM. Note that a reaction temperature of the fusion protein $PtxD_{4506}$ was 40° C., and a reaction temperature of the fusion protein $PtxD_{Pst}$ was 28° C.

Based on the measured concentration of the substrate ($NAD^+$) and the measured production rate of NADH, values of Km (μM), Vmax (μmol/min/m), Kcat ($min^{-1}$), and Kcat/km were calculated in accordance with a well-known enzyme kinetic method (see, for example, "Fundamental Experiment Method of Proteins and Enzymes (2nd revised edition), Nankodo Co., Ltd."). Note that the experiment was carried out three times, and values of Km, Vmax, Kcat, and Kcat/km were calculated in each of the experiments. Then, for each of Km, Vmax, Kcat, and Kcat/km, an average of the values calculated in the three experiments was obtained and defined as the value of each of Km, Vmax, Kcat, and Kcat/km. Kcat was calculated by the formula: Kcat=Vmax (μmol/min/mg)×(MW/$10^3$).

Results of the experiments are shown in the following Table 1.

TABLE 1

| Protein [MW] | Experiment # | Data | Km (μM) | Vmax (μmol/min/mg) | Kcat ($min^{-1}$) | Kcat/Km |
|---|---|---|---|---|---|---|
| $PtxD_{Pst.}$ (MW: 39904) | 1 | 110326 | 74.4 | 4.9 | 194.1 | 2.6 |
| | 2 | 110329 | 71.2 | 4.1 | 163.9 | 2.3 |
| | 3 | 110330 | 74.7 | 3.8 | 150.8 | 2.0 |
| | average | | 73.4 | 4.2 | 169.6 | 2.3 |
| | SD | | 1.9 | 0.6 | 22.2 | 0.3 |
| $PtxD_{4506}$ (MW: 40076) | 1 | 110326 | 22.6 | 6.4 | 255.7 | 11.3 |
| | 2 | 110329 | 23.3 | 6.1 | 244.1 | 10.5 |
| | 3 | 110330 | 25.1 | 5.3 | 212.4 | 8.5 |
| | average | | 23.7 | 5.9 | 237.4 | 10.1 |
| | SD | | 1.3 | 0.6 | 22.4 | 1.6 |

As is clear from Table 1, Km of $PtxD_{4506}$ was about a third of that of $PtxD_{Pst}$. Vmax of $PtxD_{4506}$ was about 1.4 times that of $PtxD_{Pst}$. Kcat of $PtxD_{4506}$ was 237.4 ($min^{-1}$), and Kcat of $PtxD_{Pst}$ was 169.6 ($min^{-1}$).

From the above experimental data, it became clear that Kcat/km of $PtxD_{4506}$ is about 4.4 times that of $PtxD_{Pst}$. That is, it became clear that $PtxD_{4506}$ has reaction efficiency higher than that of $PtxD_{Pst}$.

6. Activity of Phosphite Dehydrogenase Protein in the Presence of Inhibitor $PtxD_{4506}$ and $PtxD_{Pst}$, which were purified with use of the HisTrap column in [3. Expression of Phosphite Dehydrogenase Protein By Using *Escherichia Coli*], were examined in terms of whether or not $PtxD_{4506}$ and $PtxD_{Pst}$ would be able to exhibit a catalytic activity in the presence of various inhibitors. An experimental method was based on a method described in the literature "Costas et al., Journal of Biological Chemistry, 2001, 276, 17429-17436." The experimental method is briefly described below.

A reaction solution was prepared by mixing 100 µL of 100 mM MOPS-KOH (pH 7.25), 50 µL of 10 mM NAD, 5 µL of 5 mM phosphite, 50 µL of 40 mM inhibitor of various kinds (arsenite, nitrate, sulfate, or NaCl), 294 µL of $H_2O$, and 1 µL of 0.5 mg/mL protein-containing solution (a $PtxD_{4506}$-containing solution, a $PtxD_{Pst}$-containing solution, or a liquid which contained no protein (negative control)).

The reaction solution was reacted for 60 minutes. Note that the reaction solution containing the $PtxD_{4506}$-containing solution was reacted at 45° C., and the reaction solution containing the $PtxD_{Pst}$-containing solution was reacted at 30° C. Subsequently, $OD_{340}$ was measured. A relative value of $OD_{340}$ of each sample was calculated relative to 100 of a value of $OD_{340}$ of the reaction solution containing the liquid which contained no protein (negative control). Note that each experiment was conducted 4 times or more, and an average of relative values obtained in the 4 or 5 experiments was also calculated.

Results of the experiments are shown in the following Table 2, and the numerical data in Table 2 are shown in a graph of FIG. 4.

TABLE 2

|  |  | 1 | 2 | 3 | 4 | 5 | average | SD |
|---|---|---|---|---|---|---|---|---|
| $PtxD_{4506}$ | no inhibitor | 100.0 | 100.0 | 100.0 | 100.0 | 100.0 | 100.0 | 0.0 |
|  | Arsenite | 102.6 | 102.2 | 101.7 | 101.3 | 100.2 | 101.6 | 0.9 |
|  | Nitrate | 29.2 | 39.6 | 40.2 | 40.3 | 29.3 | 35.7 | 5.9 |
|  | Sulfite | — | 53.2 | 58.8 | 57.0 | 40.9 | 52.5 | 8.1 |
|  | NaCl | 92.6 | 96.9 | 95.7 | 95.9 | 87.1 | 93.6 | 4.0 |
| $PtxD_{Pst}$ | no inhibitor | 100.0 | 100.0 | 100.0 | 100.0 | 100.0 | 100.0 | 0.0 |
|  | Arsenite | 82.3 | 90.4 | 88.6 | 91.4 | 90.7 | 86.6 | 4.8 |

TABLE 2-continued

|  | 1 | 2 | 3 | 4 | 5 | average | SD |
|---|---|---|---|---|---|---|---|
| Nitrate | 15.3 | 21.8 | 20.3 | 20.1 | 14.0 | 18.3 | 3.4 |
| Sulfite | — | 15.4 | 15.3 | 16.2 | 9.2 | 14.0 | 3.3 |
| NaCl | 95.2 | 91.8 | 36.0 | 84.2 | 76.7 | 89.3 | 5.1 |

["—" in the table shows that no data was obtained.]

Figure 4:
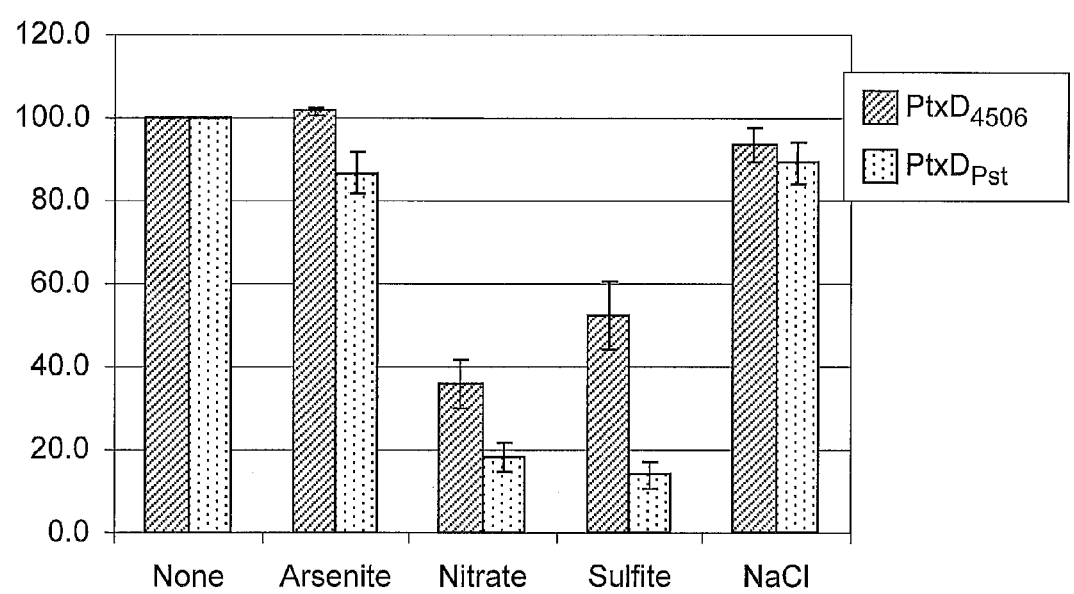
FIG. 4 is a graph showing effects of various inhibitors on an activity of a phosphite dehydrogenase protein of the present invention.

As is clear from Table 2 and FIG. 4, it became clear that an activity of $PtxD_{Pst}$ is inhibited in the presence of arsenite, nitrate, sulfate, or NaCl.

On the other hand, it became clear that an activity of $PtxD_{4506}$ is maintained in a high level even in the presence of arsenite, nitrate, sulfate, or NaCl. This shows that it is advantageous to use $PtxD_{4506}$ in a case where phosphite dehydrogenase needs to be used in the presence of arsenite, nitrate, sulfate, or NaCl (particularly in the presence of arsenite, nitrate, or sulfate). Examples of a case in which phosphite dehydrogenase needs to be used encompass a case in which NADH is produced, a case in which NADPH is produced, a case in which phosphorous acid is quantified, and the like, but are not limited to these.

The present invention is not limited to the above-described arrangements but allows various modifications within the scope of the claims. Any embodiment and example obtained by appropriately combining the technical means disclosed in the different embodiments and examples will also be included in the technical scope of the present invention.

INDUSTRIAL APPLICABILITY

The present invention can be applied to the field of producing NADH or NADPH. Further, the present invention can be applied to the field of quantifying phosphorous acid.

The invention claimed is:

1. A method for producing a phosphite dehydrogenase protein, comprising the steps of:
   (a) causing a protein to be expressed in a host; and
   (b) solubilizing, in a solution, the protein expressed in the host,
   the protein being the following (A):
   (A) a protein consisting of the amino acid sequence of SEQ ID NO: 1.

2. The method as set forth in claim 1, wherein:
   the step (a) includes a step of introducing, into the host, a vector including a gene encoding a protein of the following (A):
   (A) a protein consisting of the amino acid sequence of SEQ ID NO: 1,
   or a gene consisting of DNA of the following (C):
   (C) DNA consisting of the base sequence of SEQ ID NO: 2.

3. The method as set forth in claim 1, wherein:
   the step (b) includes a step of disrupting the host, in which the protein is expressed, into fragments in a solution containing at least one of (i) not less than 0 (w/v) but not more than 0.1% (w/v) of a surfactant and (ii) not less than 0 (w/v) but not more than 50 mM of NaCl.

4. The method as set forth in claim 3, wherein:
   the surfactant is Tween-20 or Triton-X100.

5. A method as set forth in claim 1, further comprising the step of:

(c) heating (i) the host in which the protein is expressed or (ii) the fragments of the host in which the protein is expressed.

6. The method as set forth in claim 5, wherein:

the step (c) is a step of heating, to a temperature in a range of 40° C. to 50° C., the host in which the protein is expressed or the fragments of the host in which the protein is expressed.

7. A method for producing NADH or NADPH, comprising:

reacting $NAD^+$ or $NADP^+$ with $HPO_3^{2-}$ and $H_2O$ by using, as an enzyme, a phosphite dehydrogenase protein produced by a method recited in claim 1.

8. The method as set forth in claim 7, wherein:

the reaction is carried out at a temperature in a range of 40° C. to 50° C.

9. The method as set forth in claim 7, wherein:

the reaction is carried out in the presence of arsenite, nitrate, sulfate, or NaCl.

10. The method as set forth claim 1, wherein:

the step (b) includes a step of disrupting the host, in which the protein is expressed, into fragments in the solution and a step of centrifuging the fragments to obtain a supernatant.

* * * * *

SEQUENCE LISTING

<160> NUMBER OF SEQ ID NOS: 12

<210> SEQ ID NO 1
<211> LENGTH: 336
<212> TYPE: PRT
<213> ORGANISM: Ralstonia sp. 4506

<400> SEQUENCE: 1

Met Lys Pro Lys Val Val Leu Thr His Trp Val His Pro Glu Ile Ile
1               5                   10                  15

Glu Leu Leu Ser Ala Ser Ala Asp Val Ile Pro Asn Thr Thr Arg Glu
            20                  25                  30

Thr Leu Pro Arg Ser Glu Val Ile Ala Arg Ala Lys Asp Ala Asp Ala
        35                  40                  45

Leu Met Ala Phe Met Pro Asp Ser Ile Asp Ser Ala Phe Leu Glu Glu
    50                  55                  60

Cys Pro Lys Leu Arg Val Ile Gly Ala Ala Leu Lys Gly Tyr Asp Asn
65                  70                  75                  80

Phe Asp Val Asn Ala Cys Thr Arg His Gly Val Trp Leu Thr Ile Val
                85                  90                  95

Pro Asp Leu Leu Thr Ile Pro Thr Ala Glu Leu Thr Ile Gly Leu Leu
            100                 105                 110

Leu Gly Leu Thr Arg His Met Leu Glu Gly Asp Arg Gln Ile Arg Ser
        115                 120                 125

Gly His Phe Gln Gly Trp Arg Pro Thr Leu Tyr Gly Ser Gly Leu Thr
    130                 135                 140

```
Gly Lys Thr Leu Gly Ile Ile Gly Met Gly Ala Val Gly Arg Ala Ile
145                 150                 155                 160

Ala Gln Arg Leu Ala Gly Phe Glu Met Asn Leu Leu Tyr Cys Asp Pro
                165                 170                 175

Ile Pro Leu Asn Ala Glu Gln Glu Lys Ala Trp His Val Gln Arg Val
            180                 185                 190

Thr Leu Asp Glu Leu Leu Glu Lys Cys Asp Tyr Val Val Pro Met Val
        195                 200                 205

Pro Met Ala Ala Glu Thr Leu His Leu Ile Asp Ala Thr Ala Leu Ala
210                 215                 220

Lys Met Lys Thr Gly Ser Tyr Leu Ile Asn Ala Cys Arg Gly Ser Val
225                 230                 235                 240

Val Asp Glu Asn Ala Val Ile Ala Ala Leu Ala Ser Gly Lys Leu Ala
                245                 250                 255

Gly Tyr Ala Ala Asp Val Phe Glu Met Glu Glu Trp Ile Arg Ala Asp
            260                 265                 270

Arg Pro Gln Ala Ile Pro Lys Ala Leu Leu Asp Asn Thr Ala Gln Thr
        275                 280                 285

Phe Phe Thr Pro His Leu Gly Ser Ala Val Lys Glu Val Arg Leu Glu
290                 295                 300

Ile Glu Arg Gln Ala Ala Met Asn Ile Ile Gln Ala Leu Ala Gly Glu
305                 310                 315                 320

Lys Pro Met Gly Ala Ile Asn Gln Pro Tyr Pro Gly Val Lys Ala Ala
                325                 330                 335

<210> SEQ ID NO 2
<211> LENGTH: 1011
<212> TYPE: DNA
<213> ORGANISM: Ralstonia sp. 4506

<400> SEQUENCE: 2
atgaagccca aagtcgtcct cacccactgg gtgcacccgg aaatcatcga attgttgtcc      60
gctagcgccg atgttatccc caacaccaca cgggaaacct tgccgcgttc tgaggtaatt     120
gcgcgagcca aagatgcgga tgcactcatg gctttcatgc cggacagcat cgacagcgcg     180
tttctcgagg aatgtccaaa gctgcgtgtc atcggcgccg cgcttaaagg ctatgataac     240
ttcgatgtca acgcctgcac acgccacggt gtatggctta cgattgtgcc ggatttgctt     300
acgatcccga ccgctgaact gactatcggc cttcttctcg gtttgacaag gcatatgctg     360
gaaggcgata ggcaaatccg tagcggacac ttccaaggct ggcggccgac actatatggc     420
tctggtttga caggaaaaac gcttggcatc attggtatgg gggcggtcgg ccgtgcaatc     480
gcccagcgct ggctggcttt gaaatgaat ctcttgtatt gcgatccgat tccgctcaat      540
gccgaacaag aaaaggcttg gcacgtacag gcgtcacgc tcgatgaact gctcgaaaaa     600
tgtgattatg tcgtgccgat ggttccgatg gccgcagaga cactgcatct gatcgatgcc     660
accgcgttgg ccaagatgaa aaccggtagc tacctgatca atgcatgtcg cggctcggtc     720
gtggatgaga atgcggtgat agcagcactg gcgtctggaa aactagctgg atatgcagcc     780
gatgtcttcg agatggaaga atggatacg gctgatcgcc gcaggctat ccccaaggcg      840 ctgctcgaca atacggcaca aacgtttttt acgccgcatt tgggatcggc ggtcaaggaa     900
gttcggcttg aaatcgagcg gcaggcagcg atgaacatca tccaggcact cgctggtgaa     960
aaaccgatgg gcgcgattaa tcagccgtat ccgggagtaa aggcggcgtg a             1011
```

<210> SEQ ID NO 3
<211> LENGTH: 336
<212> TYPE: PRT
<213> ORGANISM: Pseudomonas stutzeri

<400> SEQUENCE: 3

Met Leu Pro Lys Leu Val Ile Thr His Arg Val His Asp Glu Ile Leu
1               5                   10                  15

Gln Leu Leu Ala Pro His Cys Glu Leu Met Thr Asn Gln Thr Asp Ser
            20                  25                  30

Thr Leu Thr Arg Glu Glu Ile Leu Arg Arg Cys Arg Asp Ala Gln Ala
        35                  40                  45

Met Met Ala Phe Met Pro Asp Arg Val Asp Ala Asp Phe Leu Gln Ala
    50                  55                  60

Cys Pro Glu Leu Arg Val Val Gly Cys Ala Leu Lys Gly Phe Asp Asn
65                  70                  75                  80

Phe Asp Val Asp Ala Cys Thr Ala Arg Gly Val Trp Leu Thr Phe Val
                85                  90                  95

Pro Asp Leu Leu Thr Val Pro Thr Ala Glu Leu Ala Ile Gly Leu Ala
            100                 105                 110

Val Gly Leu Gly Arg His Leu Arg Ala Ala Asp Ala Phe Val Arg Ser
        115                 120                 125

Gly Glu Phe Gln Gly Trp Gln Pro Gln Phe Tyr Gly Thr Gly Leu Asp
    130                 135                 140

Asn Ala Thr Val Gly Ile Leu Gly Met Gly Ala Ile Gly Leu Ala Met
145                 150                 155                 160

Ala Asp Arg Leu Gln Gly Trp Gly Ala Thr Leu Gln Tyr His Glu Ala
                165                 170                 175

Lys Ala Leu Asp Thr Gln Thr Glu Gln Arg Leu Gly Leu Arg Gln Val
            180                 185                 190

Ala Cys Ser Glu Leu Phe Ala Ser Ser Asp Phe Ile Leu Leu Ala Leu
        195                 200                 205

Pro Leu Asn Ala Asp Thr Gln His Leu Val Asn Ala Glu Leu Leu Ala
    210                 215                 220

Leu Val Arg Pro Gly Ala Leu Leu Val Asn Pro Cys Arg Gly Ser Val
225                 230                 235                 240

Val Asp Glu Ala Ala Val Leu Ala Ala Leu Glu Arg Gly Gln Leu Gly
                245                 250                 255

Gly Tyr Ala Ala Asp Val Phe Glu Met Glu Asp Trp Ala Arg Ala Asp
            260                 265                 270

Arg Pro Arg Leu Ile Asp Pro Ala Leu Leu Ala His Pro Asn Thr Leu
        275                 280                 285

Phe Thr Pro His Ile Gly Ser Ala Val Arg Ala Val Arg Leu Glu Ile
    290                 295                 300

Glu Arg Cys Ala Ala Gln Asn Ile Ile Gln Val Leu Ala Gly Ala Arg
305                 310                 315                 320

Pro Ile Asn Ala Ala Asn Arg Leu Pro Lys Ala Glu Pro Ala Ala Cys
                325                 330                 335

<210> SEQ ID NO 4
<211> LENGTH: 1011
<212> TYPE: DNA
<213> ORGANISM: Pseudomonas stutzeri

<400> SEQUENCE: 4

```
atgctgccga aactcgttat aactcaccga gtacacgatg agatcctgca actgctggcg      60
ccacattgcg agctgatgac caaccagacc gacagcacgc tgacgcgcga ggaaattctg     120
cgccgctgtc gcgatgctca ggcgatgatg gcgttcatgc ccgatcgggt cgatgcagac     180
tttcttcaag cctgccctga gctgcgtgta gtcggctgcg cgctcaaggg cttcgacaat     240
ttcgatgtgg acgcctgtac tgcccgcggg gtctggctga ccttcgtgcc tgatctgttg     300
acggtcccga ctgccgagct ggcgatcgga ctggcggtgg ggctggggcg catctgcgg      360 gcagcagatg cgttcgtccg ctctggcgag ttccagggct ggcaaccaca gttctacggc     420
acggggctgg ataacgctac ggtcggcatc cttggcatgg gcgccatcgg actggccatg     480
gctgatcgct tgcagggatg gggcgcgacc ctgcagtacc acgaggcgaa ggctctggat     540
acacaaaccg agcaacggct cggcctgcgc caggtggcgt gcagcgaact cttcgccagc     600
tcggacttca tcctgctggc gcttcccttg aatgccgata cccagcatct ggtcaacgcc     660
gagctgcttg ccctcgtacg gccgggcgct ctgcttgtaa accctgtcg tggttcggta      720 gtggatgaag ccgccgtgct cgcggcgctt gagcgaggcc agctcggcgg gtatgcggcg     780
gatgtattcg aaatggaaga ctgggctcgc gcggaccggc cgcggctgat cgatcctgcg     840
ctgctcgcgc atccgaatac gctgttcact ccgcacatag ggtcggcagt gcgcgcggtg     900
cgcctggaga ttgaacgttg tgcagcgcag aacatcatcc aggtattggc aggtgcgcgc     960
ccaatcaacg ctgcgaaccg tctgcccaag gccgagcctg ccgcatgttg a            1011
```

<210> SEQ ID NO 5
<211> LENGTH: 20
<212> TYPE: DNA
<213> ORGANISM: Artificial Sequence
<220> FEATURE:
<223> OTHER INFORMATION: Artificially Synthesized Sequence

<400> SEQUENCE: 5

```
agagtttgat cctggctcag                                                 20
```

<210> SEQ ID NO 6
<211> LENGTH: 19
<212> TYPE: DNA
<213> ORGANISM: Artificial Sequence
<220> FEATURE:
<223> OTHER INFORMATION: Artificially Synthesized Sequence

<400> SEQUENCE: 6

```
gtcccgcaac gagcgcaac                                                  19
```

<210> SEQ ID NO 7
<211> LENGTH: 21
<212> TYPE: DNA
<213> ORGANISM: Artificial Sequence
<220> FEATURE:
<223> OTHER INFORMATION: Artificially Synthesized Sequence
<220> FEATURE:
<221> NAME/KEY: misc_feature
<222> LOCATION: (6)..(6)
<223> OTHER INFORMATION: n is a, c, g, or t

<400> SEQUENCE: 7

```
aarggntayg ayaayttyga y                                               21
```

<210> SEQ ID NO 8
<211> LENGTH: 21
<212> TYPE: DNA
<213> ORGANISM: Artificial Sequence

```
<220> FEATURE:
<223> OTHER INFORMATION: Artificially Synthesized Sequence
<220> FEATURE:
<221> NAME/KEY: misc_feature
<222> LOCATION: (16)..(16)
<223> OTHER INFORMATION: n is a, c, g, or t

<400> SEQUENCE: 8
rtcytccaty tcrtanacrt c                                              21

<210> SEQ ID NO 9
<211> LENGTH: 25
<212> TYPE: DNA
<213> ORGANISM: Artificial Sequence
<220> FEATURE:
<223> OTHER INFORMATION: Artificially Synthesized Sequence

<400> SEQUENCE: 9
tcgtggatga gaatgcggtg atagc                                          25

<210> SEQ ID NO 10
<211> LENGTH: 25
<212> TYPE: DNA
<213> ORGANISM: Artificial Sequence
<220> FEATURE:
<223> OTHER INFORMATION: Artificially Synthesized Sequence

<400> SEQUENCE: 10
atagtcagtt cagcggtcgg gatcg                                          25

<210> SEQ ID NO 11
<211> LENGTH: 30
<212> TYPE: DNA
<213> ORGANISM: Artificial Sequence
<220> FEATURE:
<223> OTHER INFORMATION: Artificially Synthesized Sequence

<400> SEQUENCE: 11
cgggatccga tgaagcccaa agtcgtcctc                                     30

<210> SEQ ID NO 12
<211> LENGTH: 29
<212> TYPE: DNA
<213> ORGANISM: Artificial Sequence
<220> FEATURE:
<223> OTHER INFORMATION: Artificially Synthesized Sequence

<400> SEQUENCE: 12
cggaattcgc cgcctttact cccggatac                                      29
```